(12) United States Patent
Jabri et al.

(10) Patent No.: US 8,243,882 B2
(45) Date of Patent: Aug. 14, 2012

(54) SYSTEM AND METHOD FOR INDICATING ASSOCIATION BETWEEN AUTONOMOUS DETECTOR AND IMAGING SUBSYSTEM

(75) Inventors: Kadri Nizar Jabri, Oak Creek, WI (US); Gopal Biligeri Avinash, Menomonee Falls, WI (US); John Michael Sabol, Sussex, WI (US); Rajeev Ramankutty Marar, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 167 days.

(21) Appl. No.: 12/776,166

(22) Filed: May 7, 2010

(65) Prior Publication Data

US 2011/0274244 A1 Nov. 10, 2011

(51) Int. Cl.
*H05G 1/54* (2006.01)

(52) U.S. Cl. .......................................... 378/116; 378/98

(58) Field of Classification Search .................... 378/98, 378/98.8, 114–116
See application file for complete search history.

(56) References Cited

U.S. PATENT DOCUMENTS

| | | | |
|---|---|---|---|
| 5,561,611 A | 10/1996 | Avinash | |
| 5,832,134 A | 11/1998 | Avinash et al. | |
| 5,923,789 A | 7/1999 | Avinash | |
| 5,943,433 A | 8/1999 | Avinash | |
| 5,987,347 A | 11/1999 | Khoury et al. | |
| 6,100,689 A | 8/2000 | Huff et al. | |
| 6,118,846 A | 9/2000 | Liu | |
| 6,173,083 B1 | 1/2001 | Avinash | |
| 6,208,763 B1 | 3/2001 | Avinash | |
| 6,246,783 B1 | 6/2001 | Avinash | |
| 6,343,111 B1 | 1/2002 | Avinash et al. | |
| 6,354,737 B1 | 3/2002 | Hufe et al. | |
| 6,389,097 B1 | 5/2002 | Bulkes et al. | |
| 6,556,720 B1 | 4/2003 | Avinash | |
| 6,574,304 B1 | 6/2003 | Hsieh et al. | |
| 6,579,239 B1 | 6/2003 | Avinash et al. | |
| 6,580,779 B2 | 6/2003 | Avinash et al. | |
| 6,588,151 B1 | 7/2003 | Goscicki et al. | |
| 6,592,523 B2 | 7/2003 | Avinash et al. | |
| 6,614,874 B2 | 9/2003 | Avinash | |
| 6,661,873 B2 | 12/2003 | Jabri et al. | |
| 6,687,329 B1 | 2/2004 | Hsieh et al. | |

(Continued)

FOREIGN PATENT DOCUMENTS

EP 2062533 A1 5/2009

OTHER PUBLICATIONS

U.S. Appl. No. 12/506,067, filed Jul. 20, 2009, Sabol et al.

(Continued)

*Primary Examiner* — Courtney Thomas
(74) *Attorney, Agent, or Firm* — Fletcher Yoder, P.C.

(57) ABSTRACT

A method and a system are disclosed for operating an X-ray imaging subsystem with an X-ray imaging detector. Each subsystem may be one of many that could operate with one another to create X-ray images. An association is established between the imaging subsystem and the imaging detector, and a user-perceptible indication of the association is generated. The user may be prompted to confirm the association. Thereafter, the two subsystems may be used together for X-ray imaging. An X-ray source of the imaging subsystem may be disabled until the association is established or until the confirmation is received.

25 Claims, 7 Drawing Sheets

U.S. PATENT DOCUMENTS

| | | |
|---|---|---|
| 6,701,025 B1 | 3/2004 | Avinash |
| 6,721,386 B2 | 4/2004 | Bulkes et al. |
| 6,748,044 B2 | 6/2004 | Sabol et al. |
| 6,757,414 B1 | 6/2004 | Turek et al. |
| 6,757,442 B1 | 6/2004 | Avinash |
| 6,771,736 B2 | 8/2004 | Sabol et al. |
| 6,771,803 B1 | 8/2004 | Turek et al. |
| 6,771,999 B2 | 8/2004 | Salla et al. |
| 6,782,137 B1 | 8/2004 | Avinash |
| 6,792,072 B2 | 9/2004 | Avinash et al. |
| 6,813,333 B2 | 11/2004 | Karau et al. |
| 6,816,572 B2 | 11/2004 | Jabri et al. |
| 6,836,528 B2 | 12/2004 | Reddy et al. |
| 6,847,336 B1 | 1/2005 | Lemelson et al. |
| 6,898,263 B2 | 5/2005 | Avinash et al. |
| 6,917,697 B2 | 7/2005 | Avinash et al. |
| 6,942,621 B2 | 9/2005 | Avinash et al. |
| 6,954,516 B2 | 10/2005 | Li et al. |
| 6,963,670 B2 | 11/2005 | Avinash et al. |
| 6,973,219 B2 | 12/2005 | Avinash et al. |
| 6,980,624 B2 | 12/2005 | Li et al. |
| 6,980,682 B1 | 12/2005 | Avinash et al. |
| 6,996,205 B2 | 2/2006 | Capolunghi et al. |
| 6,999,549 B2 | 2/2006 | Sabol et al. |
| 7,016,467 B2 | 3/2006 | Brooks |
| 7,020,343 B1 | 3/2006 | Avinash |
| 7,050,615 B2 | 5/2006 | Avinash et al. |
| 7,056,020 B2 | 6/2006 | Saunders et al. |
| 7,056,707 B2 | 6/2006 | Sattur et al. |
| 7,058,155 B2 | 6/2006 | Piacsek et al. |
| 7,068,826 B2 | 6/2006 | Jabri et al. |
| 7,072,435 B2 | 7/2006 | Metz et al. |
| 7,169,925 B2 | 1/2007 | Merriman et al. |
| 7,187,790 B2 | 3/2007 | Sabol et al. |
| 7,194,145 B2 | 3/2007 | Avinash et al. |
| 7,206,101 B2 | 4/2007 | Avinash |
| 7,206,460 B2 | 4/2007 | Avinash et al. |
| 7,248,749 B2 | 7/2007 | Avinash et al. |
| 7,254,261 B2 | 8/2007 | Avinash et al. |
| 7,261,465 B2 | 8/2007 | Butzine et al. |
| 7,263,214 B2 | 8/2007 | Uppaluri et al. |
| 7,272,429 B2 | 9/2007 | Walker et al. |
| 7,274,811 B2 | 9/2007 | Sirohey et al. |
| 7,295,691 B2 | 11/2007 | Uppaluri et al. |
| 7,298,825 B2 | 11/2007 | Omernick et al. |
| 7,310,436 B2 | 12/2007 | Li et al. |
| 7,324,628 B2 | 1/2008 | Liu et al. |
| 7,352,885 B2 | 4/2008 | Eberhard et al. |
| 7,359,535 B2 | 4/2008 | Salla et al. |
| 7,359,540 B2 | 4/2008 | Avinash et al. |
| 7,367,953 B2 | 5/2008 | Salla et al. |
| 7,389,136 B2 | 6/2008 | Avinash et al. |
| 7,397,886 B2 | 7/2008 | Avinash et al. |
| 7,414,565 B2 | 8/2008 | Liu et al. |
| 7,415,146 B2 | 8/2008 | Unger et al. |
| 7,418,076 B2 | 8/2008 | Li et al. |
| 7,418,120 B2 | 8/2008 | Weiner et al. |
| 7,433,507 B2 | 10/2008 | Jabri et al. |
| 7,440,603 B2 | 10/2008 | Eberhard et al. |
| 7,450,747 B2 | 11/2008 | Jabri et al. |
| 7,457,451 B2 | 11/2008 | Hsieh et al. |
| 7,488,947 B1 | 2/2009 | Petrick et al. |
| 7,489,825 B2 | 2/2009 | Sirohey et al. |
| 7,490,085 B2 | 2/2009 | Walker et al. |
| 7,492,931 B2 | 2/2009 | Sabol et al. |
| 7,502,444 B2 | 3/2009 | Marer |
| 7,508,970 B2 | 3/2009 | Jabri et al. |
| 7,512,284 B2 | 3/2009 | Avinash et al. |
| 7,519,156 B2 | 4/2009 | Marer |
| 7,522,755 B2 | 4/2009 | Avinash et al. |
| 7,574,032 B2 | 8/2009 | Sirohey et al. |
| 7,575,375 B2 | 8/2009 | Marer et al. |
| 7,590,306 B2 | 9/2009 | Lal et al. |
| 7,599,579 B2 | 10/2009 | Avinash et al. |
| 7,613,478 B2 | 11/2009 | Jabri et al. |
| 7,620,227 B2 | 11/2009 | Gering et al. |
| 7,623,723 B2 | 11/2009 | Avinash et al. |
| 7,623,728 B2 | 11/2009 | Avinash et al. |
| 7,627,084 B2 | 12/2009 | Jabri et al. |
| 7,627,160 B2 | 12/2009 | Avinash et al. |
| 7,649,979 B2 | 1/2010 | Liu et al. |
| 7,664,222 B2 | 2/2010 | Jabri et al. |
| 7,702,379 B2 | 4/2010 | Avinash et al. |
| 2003/0036693 A1 | 2/2003 | Avinash et al. |
| 2003/0194056 A1* | 10/2003 | Spahn .......................... 378/205 |
| 2003/0206662 A1 | 11/2003 | Avinash et al. |
| 2004/0022425 A1 | 2/2004 | Avinash et al. |
| 2004/0037475 A1 | 2/2004 | Avinash et al. |
| 2004/0068167 A1 | 4/2004 | Hsieh et al. |
| 2004/0101088 A1 | 5/2004 | Sabol et al. |
| 2004/0120558 A1 | 6/2004 | Sabol et al. |
| 2004/0120580 A1 | 6/2004 | Sabol et al. |
| 2004/0122702 A1 | 6/2004 | Sabol et al. |
| 2004/0122703 A1 | 6/2004 | Walker et al. |
| 2004/0122704 A1 | 6/2004 | Sabol et al. |
| 2004/0122705 A1 | 6/2004 | Sabol et al. |
| 2004/0122706 A1 | 6/2004 | Walker et al. |
| 2004/0122707 A1 | 6/2004 | Sabol et al. |
| 2004/0122708 A1 | 6/2004 | Avinash et al. |
| 2004/0122709 A1 | 6/2004 | Avinash et al. |
| 2004/0122719 A1 | 6/2004 | Sabol et al. |
| 2004/0122787 A1 | 6/2004 | Avinash et al. |
| 2004/0249314 A1 | 12/2004 | Salla et al. |
| 2004/0252873 A1 | 12/2004 | Avinash et al. |
| 2005/0005755 A1 | 1/2005 | Turvey et al. |
| 2005/0031176 A1 | 2/2005 | Hertek et al. |
| 2005/0110802 A1 | 5/2005 | Avinash et al. |
| 2005/0113670 A1 | 5/2005 | Salla et al. |
| 2005/0113671 A1 | 5/2005 | Salla et al. |
| 2005/0113672 A1 | 5/2005 | Salla et al. |
| 2005/0113674 A1 | 5/2005 | Salla et al. |
| 2005/0152587 A1 | 7/2005 | Sirohey et al. |
| 2005/0256399 A1 | 11/2005 | Sirohey et al. |
| 2006/0008174 A1 | 1/2006 | Avinash et al. |
| 2006/0018526 A1 | 1/2006 | Avinash et al. |
| 2006/0052690 A1 | 3/2006 | Sirohey et al. |
| 2006/0074713 A1 | 4/2006 | Conry et al. |
| 2006/0133283 A1 | 6/2006 | Weiner et al. |
| 2006/0136143 A1 | 6/2006 | Avinash et al. |
| 2006/0136259 A1 | 6/2006 | Weiner et al. |
| 2006/0136417 A1 | 6/2006 | Avinash et al. |
| 2006/0136466 A1 | 6/2006 | Weiner et al. |
| 2006/0136467 A1 | 6/2006 | Avinash et al. |
| 2006/0143044 A1 | 6/2006 | Conry et al. |
| 2006/0143060 A1 | 6/2006 | Conry et al. |
| 2006/0149808 A1 | 7/2006 | Weiner et al. |
| 2006/0149837 A1 | 7/2006 | Weiner et al. |
| 2006/0184489 A1 | 8/2006 | Weiner et al. |
| 2006/0188071 A1 | 8/2006 | Spahn .......................... 378/196 |
| 2006/0242146 A1 | 10/2006 | Piacsek et al. |
| 2006/0287593 A1 | 12/2006 | Jaggu et al. |
| 2006/0291711 A1 | 12/2006 | Jabri et al. |
| 2007/0036419 A1 | 2/2007 | Jabri et al. |
| 2007/0052716 A1 | 3/2007 | Jabri et al. |
| 2007/0078873 A1 | 4/2007 | Avinash et al. |
| 2007/0081699 A1 | 4/2007 | Avinash et al. |
| 2007/0081700 A1 | 4/2007 | Blumenfeld et al. |
| 2007/0081701 A1 | 4/2007 | Sirohey et al. |
| 2007/0081707 A1 | 4/2007 | Sirohey et al. |
| 2007/0116180 A1 | 5/2007 | Omernick et al. ............ 378/116 |
| 2007/0116348 A1 | 5/2007 | Jabri |
| 2007/0118399 A1 | 5/2007 | Avinash et al. |
| 2007/0127789 A1 | 6/2007 | Hoppel et al. |
| 2007/0133851 A1 | 6/2007 | Sirohey et al. |
| 2007/0156450 A1 | 7/2007 | Roehm et al. |
| 2007/0156626 A1 | 7/2007 | Roehm et al. |
| 2007/0165141 A1 | 7/2007 | Srinivas et al. |
| 2007/0165783 A1 | 7/2007 | Abu Tabanjeh ............... 378/116 |
| 2007/0165920 A1 | 7/2007 | Gering et al. |
| 2007/0286527 A1 | 12/2007 | Jabri et al. |
| 2008/0008372 A1 | 1/2008 | Li et al. |
| 2008/0008373 A1 | 1/2008 | Sirohey et al. |
| 2008/0021301 A1 | 1/2008 | Gonzalez et al. |
| 2008/0025583 A1 | 1/2008 | Jabri et al. |
| 2008/0031507 A1 | 2/2008 | Uppaluri et al. |
| 2008/0037846 A1 | 2/2008 | Avinash et al. |
| 2008/0037847 A1 | 2/2008 | Avinash et al. |

| | | |
|---|---|---|
| 2008/0064949 A1 | 3/2008 | Hertel et al. |
| 2008/0095462 A1 | 4/2008 | Hsieh et al. |
| 2008/0108895 A1 | 5/2008 | Sabol et al. |
| 2008/0118021 A1 | 5/2008 | Dutta et al. |
| 2008/0118111 A1 | 5/2008 | Sirohey et al. |
| 2008/0118121 A1 | 5/2008 | Skinner et al. |
| 2008/0118122 A1 | 5/2008 | Sirohey et al. |
| 2008/0118127 A1 | 5/2008 | Sirohey et al. |
| 2008/0118131 A1 | 5/2008 | Skinner et al. |
| 2008/0119713 A1 | 5/2008 | Le Nezet et al. |
| 2008/0122842 A1 | 5/2008 | Sirohey et al. |
| 2008/0123812 A1 | 5/2008 | Sabol et al. |
| 2008/0123912 A1 | 5/2008 | Lal et al. |
| 2008/0126118 A1 | 5/2008 | Sirohey et al. |
| 2008/0126119 A1 | 5/2008 | Sirohey et al. |
| 2008/0126120 A1 | 5/2008 | Sirohey et al. |
| 2008/0126121 A1 | 5/2008 | Sirohey et al. |
| 2008/0130965 A1 | 6/2008 | Avinash et al. |
| 2008/0137926 A1 | 6/2008 | Skinner et al. |
| 2008/0161672 A1 | 7/2008 | Marar |
| 2008/0212839 A1 | 9/2008 | Salla et al. |
| 2008/0224056 A1 | 9/2008 | Liu et al. |
| 2008/0231910 A1 | 9/2008 | Gering et al. |
| 2008/0232699 A1 | 9/2008 | Gering et al. |
| 2008/0232700 A1 | 9/2008 | Gering et al. |
| 2008/0232701 A1 | 9/2008 | Gering et al. |
| 2008/0232718 A1 | 9/2008 | Avinash et al. |
| 2008/0240343 A1 | 10/2008 | Jabri et al. |
| 2008/0240357 A1 | 10/2008 | Jabri et al. |
| 2008/0240360 A1 | 10/2008 | Jabri et al. |
| 2008/0242977 A1 | 10/2008 | Sirohey et al. |
| 2008/0285711 A1 | 11/2008 | Avinash et al. |
| 2008/0296507 A1 | 12/2008 | Petrick et al. |
| 2009/0003679 A1 | 1/2009 | Ni et al. |
| 2009/0006131 A1 | 1/2009 | Unger et al. |
| 2009/0006132 A1 | 1/2009 | Avinash et al. |
| 2009/0060310 A1 | 3/2009 | Li et al. |
| 2009/0063186 A1 | 3/2009 | Marar |
| 2009/0067667 A1 | 3/2009 | Jabri et al. |
| 2009/0092307 A1 | 4/2009 | Sabol et al. |
| 2009/0103679 A1 | 4/2009 | Jabri et al. |
| 2009/0118606 A1 | 5/2009 | Jabri et al. |
| 2009/0129547 A1 | 5/2009 | Jabri et al. |
| 2009/0130983 A1 | 5/2009 | Venturino et al. |
| 2009/0136096 A1 | 5/2009 | Sirohey et al. |
| 2009/0136111 A1 | 5/2009 | Jabri et al. |
| 2009/0138279 A1 | 5/2009 | Avinash et al. |
| 2009/0169073 A1 | 7/2009 | Areste et al. |
| 2009/0169074 A1 | 7/2009 | Avinash et al. |
| 2009/0257628 A1 | 10/2009 | Ranga et al. |
| 2009/0279752 A1 | 11/2009 | Sirohey et al. |
| 2009/0279759 A1 | 11/2009 | Sirohey et al. |
| 2009/0281423 A1 | 11/2009 | Sirohey et al. |
| 2009/0290686 A1 | 11/2009 | Liu et al. |
| 2009/0290772 A1 | 11/2009 | Avinash et al. |
| 2009/0292478 A1 | 11/2009 | Avinash et al. |
| 2009/0292551 A1 | 11/2009 | Sirohey et al. |
| 2009/0292557 A1 | 11/2009 | Sirohey et al. |
| 2010/0004023 A1 | 1/2010 | Jabri et al. |
| 2010/0046705 A1 | 2/2010 | Jabri et al. |
| 2010/0082506 A1 | 4/2010 | Avinash et al. |

OTHER PUBLICATIONS

U.S. Appl. No. 12/776,207, filed May 7, 2010, Omernick et al.
Search Report from corresponding EP Application No. 11164571.9 dated Aug. 11, 2011.

* cited by examiner

SYSTEM AND METHOD FOR INDICATING ASSOCIATION BETWEEN AUTONOMOUS DETECTOR AND IMAGING SUBSYSTEM

BACKGROUND OF THE INVENTION

The present disclosure generally relates to digital imaging systems, and particularly to management of modular imaging systems.

A number of radiological imaging systems of various designs are known and are presently in use. Such systems are based upon generation of X-rays that are directed toward a subject of interest. The X-rays traverse the subject and impact a film or a digital detector. In medical diagnostic contexts, for example, such systems may be used to visualize internal tissues and diagnose patient ailments. In other contexts, parts, baggage, parcels, and other subjects may be imaged to assess their contents and for other purposes. In general, X-ray systems of the type referred to by the present disclosure may include projection X-ray systems, fluoroscopic systems, X-ray tomosynthesis systems, computed tomography systems, and various mixed or combined-modality systems that utilize X-ray imaging in conjunction with other imaging physics, such as ultrasound, positron emission tomography, magnetic resonance imaging, and so forth.

An X-ray imaging system may be portable or stationary, and may generally include imager and detection components. The imager components may include substantially stationary X-ray sources, such as would be found in an X-ray imaging room on a c-arm gantry or positioning arm, or mobile X-ray sources, such as a mobile X-ray source on wheels that may be deployed adjacent to a patient bed or similar area. The detection components may include a wired or wireless detector, which may be compatible with either of the stationary or mobile source components. However, such detectors, while portable, may only be used within one particular X-ray imaging system. That is, a single detector is typically not able to be used in different imaging systems, as it may be permanently integrated into a particular imaging system. Therefore, if a single detector subsystem can be used with multiple imaging subsystems, a hospital may be able to leverage its resources more optimally. In such systems, there is a possibility that a user, for example a radiologist or technician, may inadvertently attempt to utilize a detector that has little to no operability with a particular imager subsystem and subject a patient to unnecessary radiation. On the other hand, even if the user has compatible detector and imaging subsystems, the user has to ensure that they are associated with one another before subjecting a patient to appropriate levels of radiation.

BRIEF DESCRIPTION OF THE INVENTION

In one embodiment, a method of operation of an X-ray imaging system is provided. The method includes creating an association between an autonomous imaging subsystem and an autonomous detector subsystem. A user-viewable indication of the association is provided on the autonomous imaging subsystem, the autonomous detector subsystem, or both.

In another embodiment, a method of operation of an X-ray imaging system is provided. The method includes associating an X-ray imaging subsystem and an X-ray detector subsystem, generating a user-perceptible indication of the association, receiving a user confirmation of the association, and imaging a subject with the X-ray imaging subsystem and the X-ray detector subsystem.

In a further embodiment, an X-ray imaging system is provided. The system includes an autonomous imaging subsystem capable of operation with one or a plurality of autonomous detector subsystems, a plurality of autonomous detector subsystems capable of operation with the autonomous imaging subsystem, and wherein at least one of the autonomous imaging subsystem and the autonomous detector subsystems is configured create an operative association between the autonomous X-ray imaging subsystem and one of the autonomous detector subsystems, the association permitting wireless exchange of imaging data, and to generate a user-perceptible indication of the association.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements.

The terms "comprising," "including," and "having" are intended to be inclusive and mean that there may be additional elements other than the listed elements. Moreover, while the term "exemplary" may be used herein in connection to certain examples of aspects or embodiments of the presently disclosed technique, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

The present embodiments provide autonomous subsystems used in X-ray imaging applications, such as autonomous detectors and imagers. The present embodiments relate to such systems described in U.S. patent application Ser. No. 12/776,207 entitled "WIRELESS X-RAY DETECTOR OPERATION COORDINATION SYSTEM AND METHOD" filed on even date herewith, U.S. patent application Ser. No. 12/506,067 entitled "APPLICATION SERVER FOR USE WITH A MODULAR IMAGING SYSTEM" filed on Jul. 20, 2009, and U.S. Patent Application Publication No. US20090118606 entitled "MEDICAL IMAGING SYSTEM" filed on Nov. 2, 2007, all of which are incorporated into the present disclosure by reference in their entirety.

As autonomous detectors are introduced into an imaging environment, these detectors can be used with more than one imaging subsystem (e.g., X-ray sources, controllers, storage media). Autonomous detectors may have the ability to dynamically associate with a variety of imaging subsystems. However, at any one point in time, this association may be unique, as one imaging subsystem and one detector are typically suitable to perform a medical imaging examination. However, even in situations where autonomous detector and imaging subsystems can dynamically associate, there may be a risk that an operator or technologist may attempt to use the wrong detector (not associated with the imaging subsystem in use). That is, a detector may not be configured physically or functionally to receive radiation from an imaging subsystem, or may not be configured with proper software and/or firmware to permit transmission of imaging data generated by the detector during an imaging exposure.

Accordingly, it is now recognized that methods and systems to facilitate the association of a detector with an imaging subsystem is desirable. Additionally, such methods and systems may also be desirable to facilitate the identification of the detector that is currently associated with an imaging subsystem that will be used in a given examination process, and also to facilitate the identification of the imaging subsystem that is currently associated with the detector that will be used in a given examination process. The methods and systems may also allow a user to confirm or correct the established association therebetween.

Present embodiments are directed towards providing methods for association and systems having respective components that are capable of performing association sequences. The sequences may include acts that both a user and the system (e.g., an imaging system communicatively coupled with one or more autonomous subsystems) may perform. The acts may include creating a unique association between a detector and an imager subsystem and indicating the unique association to a user. The user (or controller) may confirm and/or correct the association where appropriate using, for example, a workstation operatively connected to the imaging components for which association is desirable.

Figure 1:
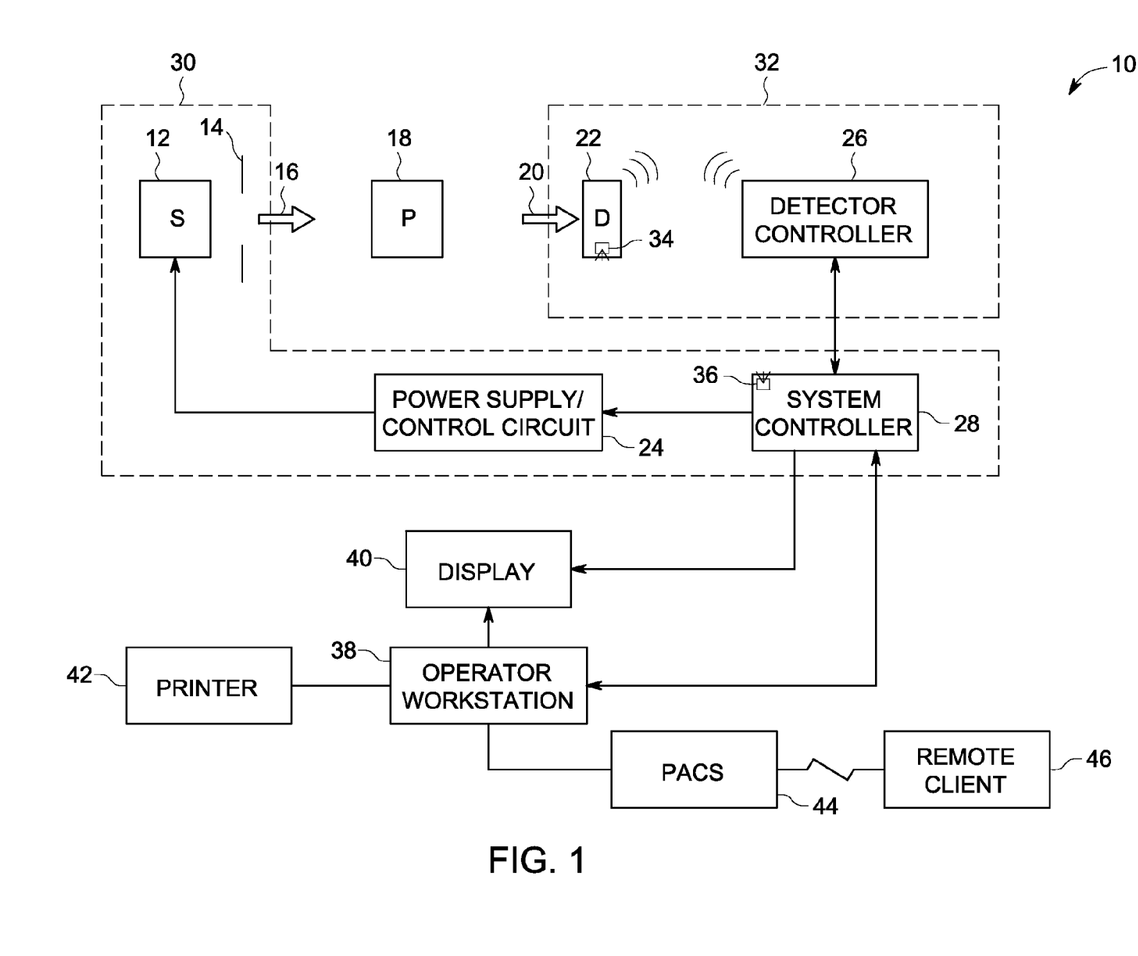
FIG. 1 is a diagrammatical overview of a digital X-ray imaging system of one embodiment in which the present embodiments may be implemented.

Turning now to the drawings, FIG. 1 illustrates diagrammatically an imaging system 10 for acquiring and processing image data. In the illustrated embodiment, the imaging system 10 is a digital X-ray system containing autonomous components. In the embodiment illustrated in FIG. 1, imaging system 10 includes a source of X-ray radiation 12 positioned adjacent to a collimator 14. The collimator 14 permits a stream of radiation 16 to pass into a region in which an object or subject, such as a patient 18, is positioned. A portion of the radiation 20 passes through or around the subject and impacts a portable digital X-ray detector 22. The detector 22 may convert the X-ray photons received on its surface to electric signals, which are acquired and processed to reconstruct an image of the features within the subject.

The radiation source 12 is controlled by a power supply/control circuit 24 which supplies both power and control signals for examination sequences. The detector 22 is communicatively coupled to a detector controller 26 which commands acquisition of the signals generated in the detector 22. In the illustrated embodiment, the detector 22 may communicate with the detector controller 26 via any suitable wire or wireless communication standard. In certain embodiments, some or all of the functions of the detector controller 26 may be integrated within a structure that also houses the detector 22, i.e., the detector controller 26 and detector 22 may be provided as a unitary device. The detector controller 26 may, among other functions, execute various signal processing and filtration functions, such as for initial adjustment of dynamic ranges, interleaving of digital image data, and so forth.

In the depicted embodiment the power supply/control circuit 24 and the detector controller 26 may communicate with, and respond to signals from, a system controller 28. In general, the system controller 28 commands operation of the imaging system to execute examination protocols and to process acquired image data. In the present context, the system controller 28 also includes signal processing circuitry (typically based upon a programmed general purpose or application-specific digital computer) and associated manufactures (such as optical memory devices, magnetic memory devices, or solid-state memory devices) for storing programs and routines executed by a processor of the computer to carry out various functionalities, as well as for storing configuration parameters and image data and so forth.

According to the approaches described herein, different components of the imaging system 10 may be provided as autonomous and separable subsystems. For example, some or all of the source 12, collimator 14, and/or power supply/control circuit 24 may be provided as an imager subsystem 30. Likewise, the detector 22 may be provided as an autonomous and separable detector subsystem 32. In the illustrated embodiment, the autonomous detector subsystem 32 includes the detector controller 26, which, as noted above, may be provided integrally with the detector 22. In other embodiments, the detector controller 26 may be provided separately from the detector 22 (such as on a downstream workstation or server or as part of the system controller 28 discussed below) or may be distributed such that aspects of the detector controller 26 are provided on the detector 22 while other aspects are provided downstream. In this manner, either of the autonomous imager subsystem 30 or the autonomous detector subsystem 32 may be exchanged for a different source or detector subsystem, having the same or different capabilities, in a dynamic imaging environment.

In the depicted embodiment, the imager subsystem 30 includes the system controller 28. However, in other embodiments, the system controller 28 may be a stand alone component or subsystem or may be part of the detector subsystem 32. In other embodiments, the functions, hardware, and/or software of the system controller 28 may be distributed so that different hardware, software, and/or firmware aspects of the system controller 28 are appropriately distributed between the imager subsystem 30, the detector subsystem 32, and/or a separate and distinct control subsystem. In this manner, the source, detection, and/or control functions of the imaging system 10 may be provided by completely or partially autonomous subsystems which can be treated as modular components, i.e., one detector subsystem 32 or imager subsystem 30 may be swapped for another to provide different respective detection or X-ray source functionality.

As used herein, the term "autonomous" describes a system or subsystem that has communication capability even when it is not connected or associated with a complementary subsystem of the imaging system 10. For example, the phrase "autonomous detector subsystem" describes a detection system that has communication capability with a network, such as server, even when it is not connected or associated with an imager subsystem 10. Further, in one embodiment, an autonomous detector subsystem 32 may provide communication capability (such as with a second autonomous imager subsystem 30 or a second network) even when it is associated with an autonomous imager subsystem 30.

Stated differently, an autonomous system component may be independently operable in terms of its system design, system implementation, application deployment, and/or service. Such autonomous components may be configured for and capable of use with more than one other complementary or counterpart autonomous component. Accordingly, in one embodiment, each of the main components (e.g., the autonomous imager subsystem 30 and the autonomous detector subsystem 32) may be considered as network nodes that operate as autonomous entities in a network environment. In such an environment, different types of autonomous imager and/or detector subsystems (such as from the same or different vendors, having the same or different capabilities and/or sizes, and so forth) can be used in various combinations in forming an imaging system 10.

In the illustrated embodiment, the imager subsystem 30 and the detector subsystem 32 communicate wirelessly, which may allow, for example, the detector 22 to be interchanged with another wireless detector where appropriate. As such, one or more components of the autonomous detector subsystem 32 and imager subsystem 30 may contain features for indicating an association therebetween. As used herein, the term "association" may be considered to denote that two or more components are linked to one another to allow imaging. The association may be wired or wireless, and may allow communication between each component as described above, for example to coordinate an imaging routine between an X-ray source, a detector, and a controller, as described below with respect to FIG. 5. The association may be performed by placing two or more subsystems in proximity, scanning one subsystem with another, scanning two or more subsystems (e.g., barcodes of each) with a separate device, and so forth, as described in further detail below. Indeed, by performing an association between the detector subsystem 32 and the imaging subsystem 30, the detector 22 of the detector subsystem 32 may be automatically configured for use with the imaging subsystem 30 as described in U.S. Pat. No. 7,298,825, entitled "PORTABLE DIGITAL DETECTOR SYSTEM", which is incorporated by reference into the present disclosure in its entirety.

An association indication may provide a user with the ability to recognize which autonomous components are associated or linked with one another. The indication may be audible, visual, tactile, or any combination of these, and may or may not be concurrent on each associated subsystem/device. In the illustrated embodiment, a visual indicator 34 is provided on the detector 22, which may be a blinking or solid-colored light, a readout of a code or other number or identifier, or a similar feature fastened to or built into the housing of the detector 22. Likewise, the imager subsystem 30 may have a visual indicator 36. In the illustrated embodiment, the visual indicator 36 is disposed on the system controller 28. However, it should be noted that the visual indicator 36 may be provided on any portion of the imager subsystem 30, such as a housing containing all of the imager subsystem's respective components. In general, the visual indicators 34 and 36 are provided in an area on each respective component to allow easy visibility to the user, are substantially the same and behave in a substantially concurrent manner (i.e., have the same colors/hues and changes thereof, blink similarly, and so on). Further, it should be noted that the indicators 34 and 36 may be substantially simultaneously affected by changes in either subsystem 30 and/or 32. Indeed, the present embodiments contemplate such associations between two or more subsystems, such as two, three, four, five or more subsystems including controllers, imagers, detectors, and so forth.

The imager subsystem 30 and/or the detector subsystem 32 may perform various functions, such as scanning operations and data acquisition in response to commands and scanning parameters provided by an operator via an operator workstation 38. From the workstation 38, the operator is able to initiate various imaging routines that are provided to the system controller 28. The workstation 38 may provide a prompt for confirming association or for completing an association sequence (such as by entering a unique code provided by the imager subsystem 30 and/or the detector subsystem 32) provided, for example, on a display 40 to which the workstation 38 is connected. Indeed, the workstation 38 may provide a central location for the user to coordinate association between various subsystems.

The display 40 also allows the operator to view relevant system data, imaging parameters, raw imaging data, reconstructed data, and so forth. Additionally, the system 10 may include a printer 42 coupled to the operator workstation 38. Further, the operator workstation 38 may include or be coupled to a picture archiving and communications system (PACS) 44. PACS 44 may be coupled to a remote system 46, radiology department information system (RIS), hospital information system (HIS) or to an internal or external network, so that others at different locations can gain access to the image data.

Figure 2:
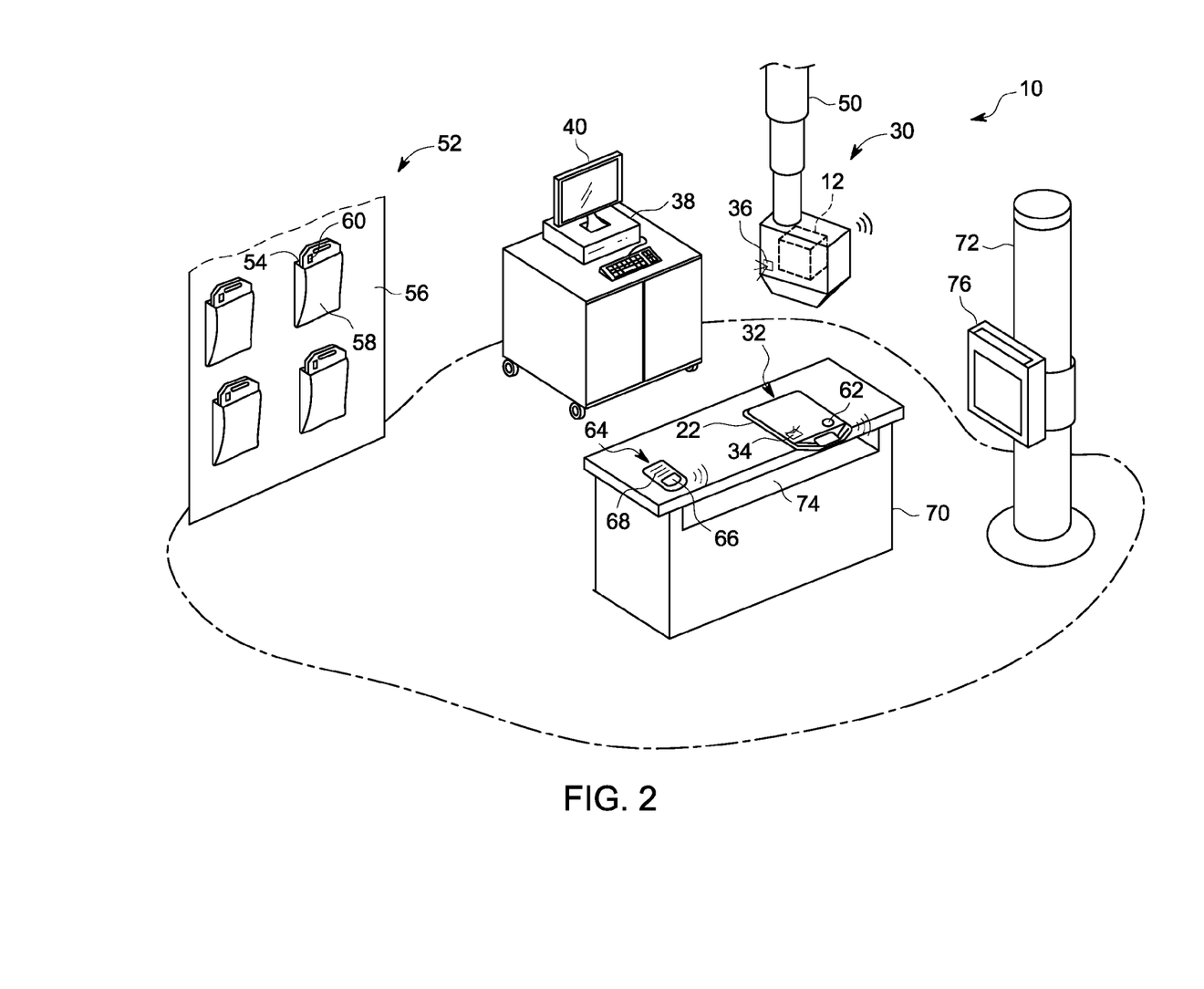
FIG. 2 is a perspective view of the digital X-ray imaging system of FIG. 1 in accordance with one embodiment.

A perspective view is provided as an example of the imaging system 10 in FIG. 2. In addition to the features described above with respect to FIG. 1, the imaging system 10 includes a positioning component in the form of an overhead tube support arm 50 for positioning the radiation source 12. In other embodiments, the radiation source 12 may be provided on a C-arm or other rotating structure to allow imaging from various angular positions. Further, in the depicted embodiment, the autonomous imager subsystem 30 may include the source 12, and may or may not include positioning subsystems (such as the arm 50 or a C-arm), power supply/control circuitry, and/or system control circuitry (such as may be provided as part of the source 12 or as part of a workstation 38 or server in communication with the source 12.

As noted above, in certain embodiments, the source 12 and/or imager subsystem 30 may receive instructions (such as from workstation 38) via a wired connection (such as an Ethernet cable) or via a wireless connection (such as via a wireless transceiver). It is noted that such a wireless transceiver included with or within each subsystem (e.g., the imaging subsystem 30 and the detector subsystem 32) may utilize any suitable wireless communication protocol, such as an ultra wideband (UWB) communication standard, a Bluetooth communication standard, or any 802.11 communication standard.

The digital detector 22 may also include one or more processor components and/or a memory device capable of storing image data acquired and/or programs, routines or protocols to be executed by the one or more processing components, such as association protocols. For example, in various embodiments, the memory device may include an optical memory device, a magnetic memory device, or a solid state-memory device containing algorithms capable of performing association processes and containing information about the detector, such as its compatibility with various imaging equipment, capabilities, design, and so forth that may be communicated to other subsystems.

In the illustrated embodiment, the association between the imaging subsystem 30 and the detector 22 is indicated via the visual indication 34 on the detector 22 and the visual indication 36 on the imaging subsystem 30. The visual indications 34 and 36 may, for example, be one color before association (e.g., red), be another color during association (e.g., yellow), and be another color when associated (e.g., green). In another embodiment, a user may confirm a provisional association between subsystems before the association sequence is complete, for example, by addressing a prompt at the workstation 38. As an example, the user may initiate the association sequence such that the imaging subsystem 30 or system controller 28, for example via recognition circuitry, wirelessly detects any portable detectors 22 within its detection range. The workstation 38 may then display the detectors 22 recognized by the imaging subsystem 30. Additionally, the user may perform an association act, such as scanning a barcode on either or both subsystems 30 and 32 or passing one or more detectors 22 in close proximity to the imaging subsystem 30 (e.g., for RFID recognition) to identify the detector 22 and imaging subsystem 30 desired for performing the imaging routine. The association indications 34 and 36 may then blink, be a certain color, or any similar indication that the particular detector 22 and imaging subsystem 30 are provisionally associated and are pending confirmation by the user. Upon confirmation by the user, for example at the workstation 38, the visual indications 34 and 36 may then blink another color, have a stable light (i.e., not blinking), be a different color, and so on. The choice of indication may depend on a number of factors, including the environment in which the imaging system 10 is deployed, other visual or audible indications or emissions from components of the subsystems, and so forth.

The association indications as well as the confirmation by the user may be desirable in situations where there are multiple detectors available for recognition and association with the imaging subsystem 30. Indeed, in embodiments where multiple wireless detectors 22 are within an operative range of the wireless capabilities of the imaging subsystem 30, a user may have difficulty in readily associating a particular portable detector 22 when no confirmation is performed. For example, the system 10 also includes a storage station 52, which is provided for storing and, in some embodiments, charging a plurality of wireless X-ray detectors 54 of varying shapes and sizes. A wall-mountable base 56 includes on its face a plurality of wireless X-ray detector storage sites 58. Therefore, the storage station 52 is adapted to receive and store a variety of different detectors 54.

Some or all of the detectors 54 stored within the storage station 52 may have wireless association capabilities. Accordingly, in situations where the storage station 52 is within wireless range of the imaging subsystem 30, some or all of the stored detectors 54 may be recognized by the imaging subsystem 30 with the ability to be associated therewith. Respective association indicators 60 may be provided for each of the stored detectors 54, such that a user may readily identify an inadvertent association, or if the user desires to use a stored detector 54 for image acquisition. In situations where the user identifies, via the association indicators 60, that an unintended association has occurred, the user may re-initiate the association, for example via the workstation 38, or directly on the portable detector 22 using an association button 62. The association button 62 may initiate, re-initiate, and/or confirm association with the imaging subsystem 30. For example, in one embodiment, the user may observe an indication on one subsystem, such as the imaging subsystem 30, and confirm the indication on the detector 22 via the association button 62.

In similar embodiments, the detector 22 and/or the imaging subsystem 30 may have a user interface for performing association. For example, in one embodiment, such as in embodiments where numbers or codes are utilized to identify each subsystem (e.g., an identifying signal), respective user interfaces may allow the user to enter or acknowledge the other subsystem's identifying code or number to confirm association. In situations where the identifying code or number of the imaging subsystem is viewed on the detector, a user may acknowledge that the code is correct or incorrect (i.e., confirm) by pressing the association button 62. In other embodiments, such as when the imaging subsystem 30 displays the identifying code or number of the detector 22, the user may confirm by pressing a similar association button (or other user-interface).

In some embodiments, a handheld device 64 may be provided for coordinating association processes. The handheld device 64, which may be a personal digital assistant (PDA) or similar device, may act as a scanning device, such as to scan respective barcodes on the imaging subsystem 30 and/or the detector subsystem 32 to create a unique association. For example, a user may scan a barcode on the imaging subsystem 30 and the detector subsystem 30, and the device 64 may communicate the identifying barcodes to the complementary subsystem for association (i.e., the detector barcode is provided to the imaging subsystem and vice-versa). The handheld device 64 may also have wireless communication circuitry such that information can be provided to and from the workstation 38 and either subsystem 30 and/or 32. The device 64 may enable remote navigation through various applications stored on the workstation 38, including association protocols such as association indication and confirmation. Accordingly, the device 64 may have a screen 66 that allows navigation through the applications of the workstation 38 and also to enables the device 64 act as a portable subsystem coordination device. The device also includes keys 68, which allows a user to input values such as uniquely indicated codes by autonomous subsystems, various commands, to create user-defined names, and so on. Indeed, the handheld device 64 may include other features such as a scanner to scan and associate each subsystem. The device 64 may also facilitate association with particular subsystems, such as one or more particular detectors 22 when multiple wireless detectors with association capability are present. Further, a user may view various information about the detector 22, such as battery charge level, current associations, capabilities, compatibilities, and so on. Information may also be displayed about the imaging subsystem 30 such as control schemes, source information such as X-ray power, imaging protocols, and the like.

One or more associated detectors 22 may be used with one or both of a patient table 70 and a stand 72 to facilitate image acquisition during an imaging protocol. Particularly, the table 70 and the stand 72 may be configured to receive one or more digital detectors 22. For instance, a digital detector 22 may be placed on the upper surface of the table 70, and the patient 18 (more specifically, an anatomy of interest of the patient 18) may be positioned on the table 70 between the detector 22 and the radiation source 12. In some other instances, one or more detectors 22 may be positioned in a slot 74 below the upper surface of the table 70 and the patient 18, or the radiation source 12 and the detector 22 may be positioned horizontally about the patient 18 for cross-table imaging. Further, the stand 72 may include a receiving structure 76 adapted to receive the digital detector 22, and the patient 18 may be positioned adjacent the stand 72 to enable image data to be acquired via the digital detector 22.

In one embodiment, the imaging system 10 may be a stationary system disposed in a fixed X-ray imaging room, such as that generally depicted in, and described above with respect to, FIG. 2. It will be appreciated, however, that the presently disclosed embodiments may also be employed with other imaging systems, including mobile X-ray units and systems. For instance, in other embodiments, a mobile X-ray unit may be moved to a patient recovery room, an emergency room, a surgical room, or the like to enable imaging of a patient without requiring transport of the patient to a dedicated (i.e., fixed) X-ray imaging room.

Figure 3:
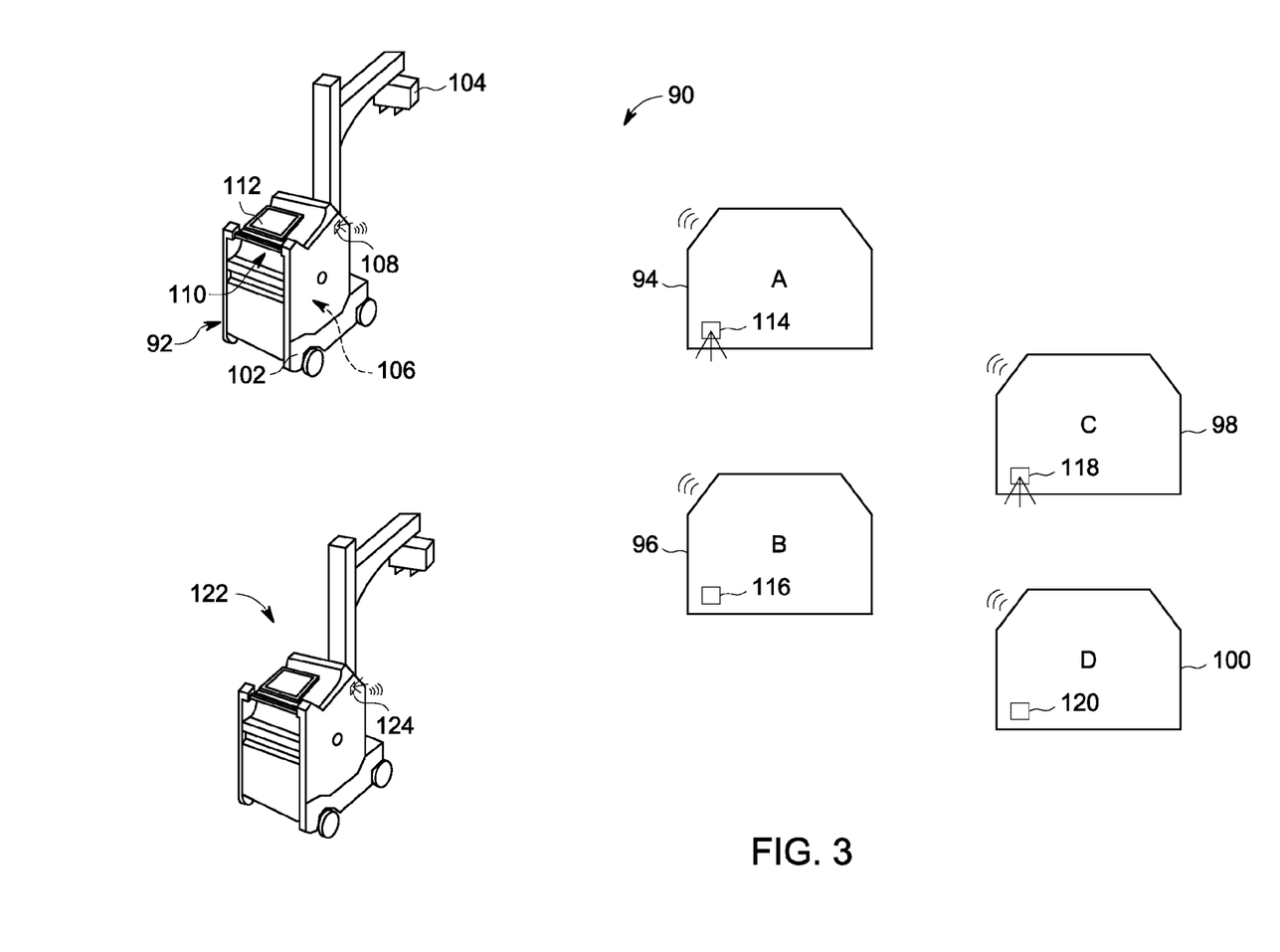
FIG. 3 is a schematic representation of multiple mobile imaging units and associated detectors, in accordance with one embodiment of the present disclosure.

One such embodiment of mobile X-ray units is illustrated in FIG. 3. In the illustrated embodiment, a mobile wireless X-ray system 90 includes a first mobile X-ray base station 92 that may recognize multiple digital X-ray detectors 94, 96, 98, and 100 located within the operative range of the first mobile X-ray base station 92. That is, the first mobile X-ray station 92 may be considered to contain the imaging subsystem 30. The first mobile X-ray base station 92 may include a wheeled base 102 that allows a user to move the mobile X-ray unit from place to place, for example from one room to another or one patient bed to another. The first mobile X-ray base station 92 has an X-ray source 104 that is used in conjunction with one or more of the digital X-ray detectors 94-100. In some embodiments, the first mobile X-ray base station 92 may communicate with the multiple X-ray detectors 94, 96, 98, and 100, as previously described in U.S. patent application Ser. No. 11/934,338, filed Nov. 2, 2007, which is hereby incorporated by reference.

The first mobile X-ray station 92 houses systems electronic circuitry 106 that recognizes (detects) the detectors 94, 96, 98 and 100 for association in addition to the processes described above. In addition, the systems electronic circuitry 106 both provides and controls power to the X-ray source 104, the wheeled base 102, and an association indicator 108 (such as via an illumination circuit) disposed on a surface of the first mobile X-ray base station 92. In the illustrated embodiment, the association indicator 108 provides a visible indication.

The first mobile X-ray base station 92 also has an operator workstation 110 coupled to a display 112. For example, the recognized detectors 94, 96, 98, and 100 are displayed on the display 112. The user may, upon initiation of an association sequence (either by the user or automatically by the system 90 after various detectors have been recognized) perform a recognition procedure as described above to associate one or more of the detectors 94, 96, 98 and 100 with the first mobile X-ray station 92.

The display 112 may have a readout of detector "A" 94, detector "B" 96, detector "C" 98, and detector "D" 100, with those that have been associated with the first mobile X-ray base station 92 being indicated as such (e.g., highlighted). Further, each of the detectors 94, 96, 98, and 100 may have respective association indicators 114, 116, 118, and 120. It should be noted that the association indicators 114, 116, 118, and 120 may perform nearly identical tasks to that of the association indicator 108 of the first mobile X-ray base station 92. In the illustrated embodiment, detector "A" 114 is depicted as providing a visual indication of association with the first mobile X-ray station 92.

In a similar manner to the first mobile X-ray station 92, a second mobile X-ray station 122 may recognize the wireless detectors 114, 116, 118, and 120. The second mobile X-ray station 122 may include similar or the same features as those described above with respect to the first mobile X-ray station 92. As such, both mobile X-ray stations may look similar or the same, and without some association indication, may be difficult to distinguish. Accordingly, it may be difficult for a user to determine which detectors have been associated with each mobile X-ray station. Therefore, by providing an association indication on each detector and X-ray station, for example the visual indication 118 on detector "C" 98 and an association indication 124 on the second mobile X-ray station 122, it may be possible to quickly determine and/or reconfigure association therebetween. For example, according to the indications shown in FIG. 3, a user may readily ascertain that detector "A" is associated with the first mobile X-ray station 92 and that the detector "C" 98 is associated with the second mobile X-ray detector.

Figure 4:
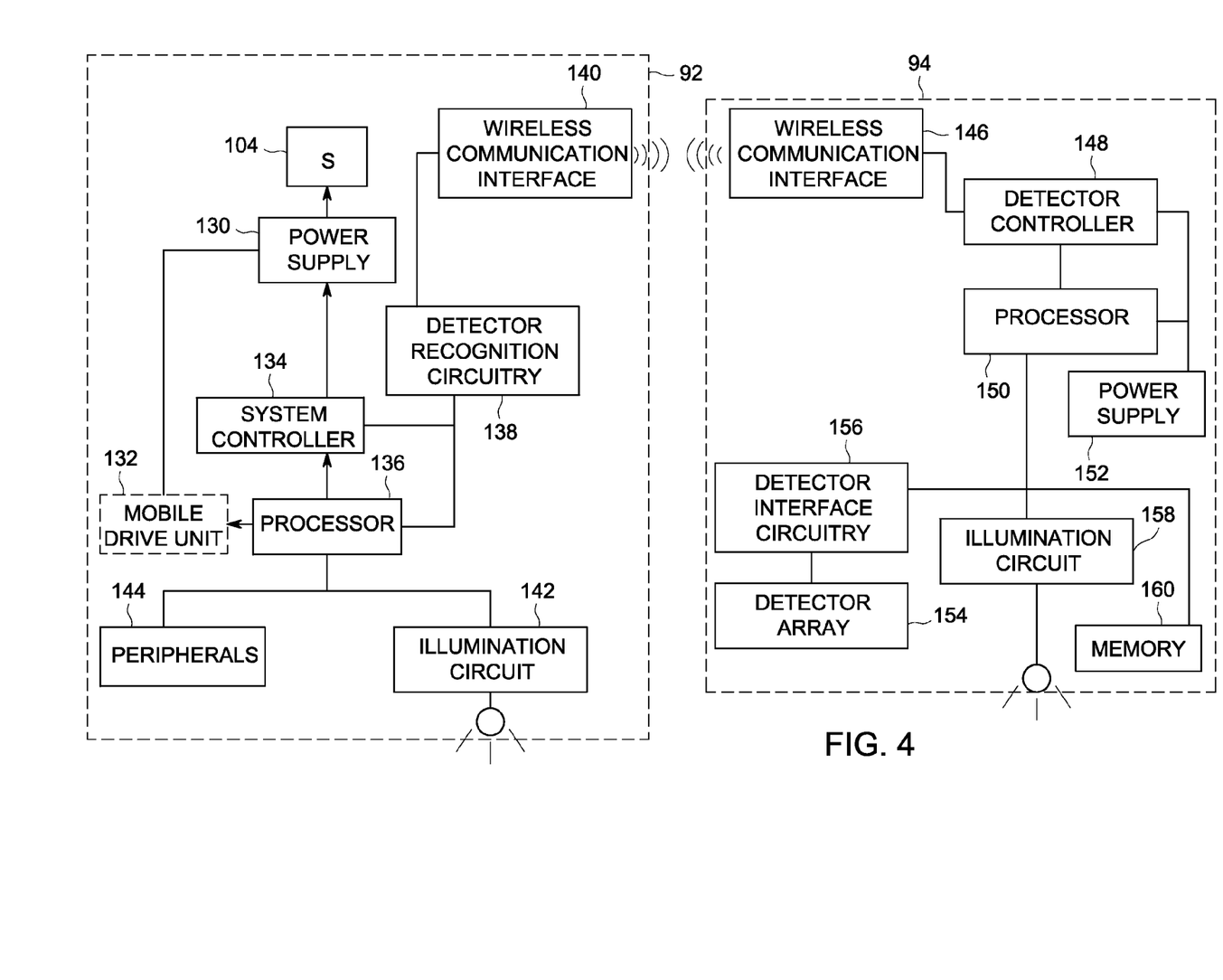
FIG. 4 is a circuit diagram of the components contained within the imaging subsystem and detector subsystem of FIGS. 1-3, in accordance with the present disclosure.

The circuitry of the wireless mobile X-ray units described above as well as the wireless detectors is illustrated diagrammatically in FIG. 4, and operates in generally the same fashion as described in FIG. 1. In addition to the tasks described above, the power supply 130 furnishes power to a mobile drive unit 132 (in embodiments of a mobile unit) of the wheeled base 106. As above, a system controller 134 commands operation of the imaging system to execute examination protocols and to process acquired image data and may include or may be responsive to a processor 136. The processor 136 also receives image data from the detector 94 and processes the data to reconstruct an image of a subject.

The processor 136 is also linked to detector recognition circuitry 138 for detecting the presence of detectors within the operative range of the first mobile X-ray base station 92. If no detector is associated or recognized within the operative range of the first mobile X-ray station 92, the processor 136 may send a signal to the system controller 134 to disable or inhibit the emission of X-rays from the X-ray source 104. The detector recognition circuitry 138 is also linked to the system controller 134. The detector recognition circuitry 138 is linked to a wireless communication interface 140 that allows wireless communication with and recognition of the detectors within the operative range of the first mobile X-ray station 92. In embodiments where the first mobile X-ray station 92 (i.e., the imager subsystem) is associated, provisionally or otherwise, with a detector, the processor 136 may send a signal to an illumination circuit 142 to activate an association indicator, such as association indicator 108 (FIG. 3). Additionally or alternatively, the first mobile X-ray station 92 may also be in communication with a server. The processor 136 is also linked to peripherals 144, which may include displays, user interfaces, memory, and so forth.

The detector 94 includes a wireless communication interface 146 for wireless communication with the first mobile X-ray station 92. The detector 94 may also be in communication with a server. It is noted that the wireless communication interface 146 may utilize any suitable wireless communication protocol, such those mentioned above with respect to FIG. 1. Moreover, detector 94 is coupled to a detector controller 148 that coordinates the control of the various detector functions. The system controller 134, as well as the detection circuitry detector recognition circuitry 138 may wirelessly provide control signals to the detector controller 148. A processor 150 that provides control signals to various detector components, the detector controller 148, and all of the circuitry depicted receive power from a power supply 152. The power supply 152 may include a battery.

Electrical signals representative of images are converted to digital values by detector interface circuitry 156, which provides the values to the processor 150 for image construction. Alternatively, the imaging data may be sent from the detector 94 to a server to process the imaging data. The processor 150 is also linked to an illumination circuit 158. The detector controller 148, in response to a signal received from the first mobile X-ray station 92, may send a signal to the processor 150 to signal the illumination circuit 158 to illuminate a light to indicate association of the detector 94 with the first mobile X-ray station 92. A memory 160 in communication with the processor 150 may store various configuration parameters, calibration files, and detector identification data. Additionally, the memory 160 may store a list of all the X-ray systems 10 with which the detector 94 is configured to operate, as well as a table that defines the compatibility of the detector 94 with specific versions of X-ray systems 10 and/or software versions.

Figure 5:
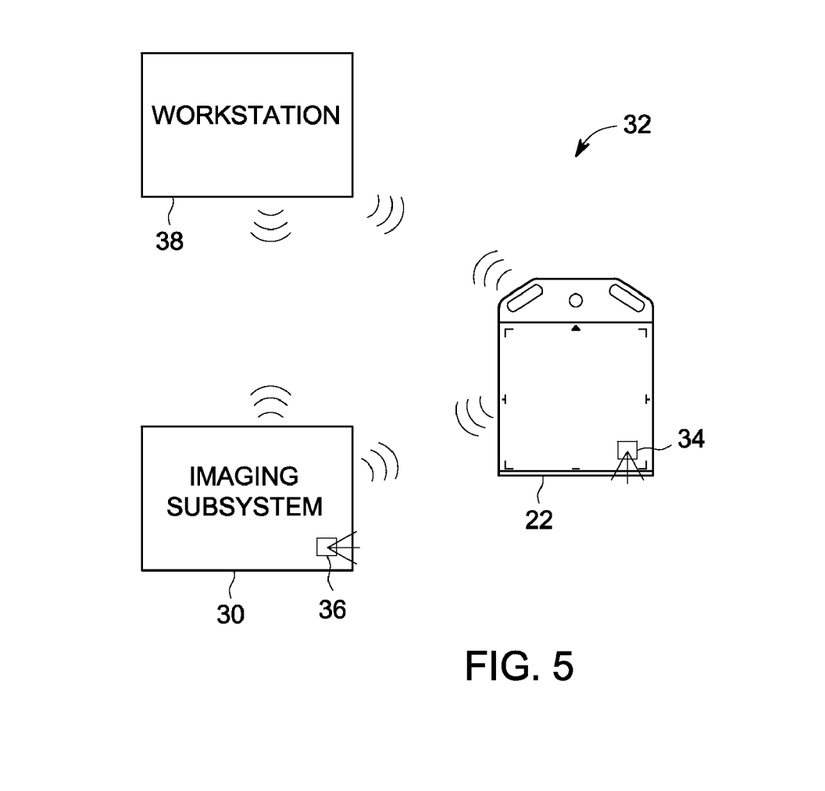
FIG. 5 is a diagrammatical overview of an embodiment of wireless communication between the workstation, imaging subsystem, and detector subsystem of FIGS. 1-4, in accordance with the present disclosure.

Such mobility of the imaging componentry may allow one or more of the autonomous imager subsystem 30, the detector subsystem 32, and/or the workstation 38 to be provided as a node on a network, such as the HIS, RIS, and/or PACS noted above. Further, each component may be mobile, wireless, and the like, such that each subsystem and/or workstation may be configured to communicate with any number of other subsystems, as illustrated in FIG. 5. In this manner, the detector subsystem 32 may communicate acquired image data to either or both of the imager subsystem 30 and the workstation 38 via a wireless network connection. Likewise, the workstation 38 may communicate with and/or control one or both of the imager subsystem 30 or the detector subsystem 32 via a wireless network connection. Similarly, the imager subsystem 30 may communicate with the workstation 38 or the detector subsystem 32 via a wireless network connection. In such a networked embodiment, the autonomous components (e.g., the imager subsystem 30, the detector subsystem 32, and the workstation 38) may operate independently and thus may communicate among themselves or with other devices on the network independent of one another. According to the approaches described herein, the imaging system 30 includes the association indicator 36 to provide a user with indicia that one or more detectors are wirelessly associated therewith. Similarly, the detector subsystem 32 has the association indicator 34 that provides indicia that the detector 22 is associated with the imaging subsystem 30. As noted above, the workstation 38 may provide information regarding a local network (e.g., associated subsystems) via a display.

Figure 6:
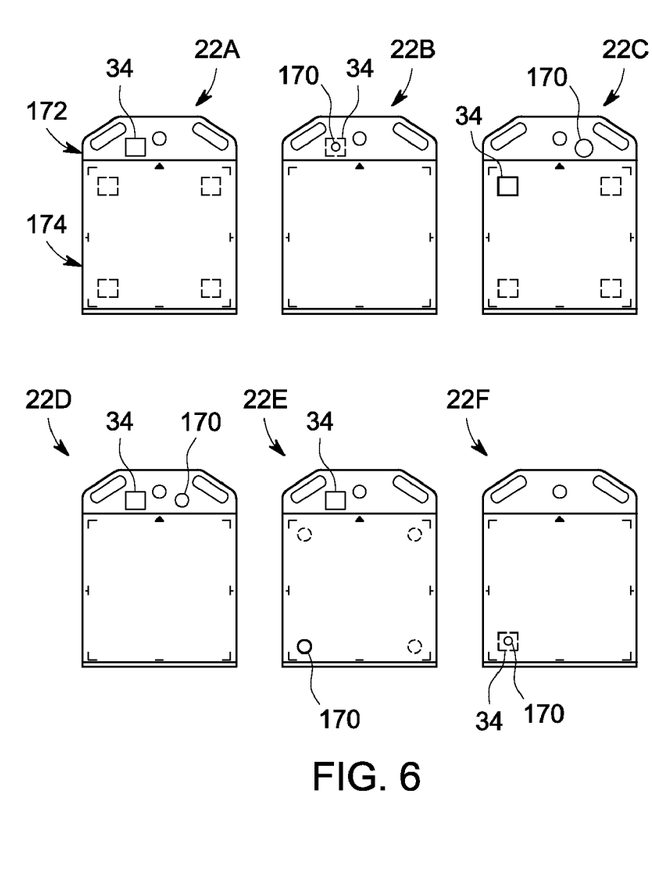
FIG. 6 is a schematic representation of the placement of association indicators and/or association buttons on or within the detector of FIGS. 1-4, in accordance with the present disclosure.

The present embodiments contemplate the placement of an association indicator and, optionally, an association button (e.g., to initiate, confirm, or re-initiate association) on various locations of the wireless detector 22. FIG. 6 illustrates several examples of detectors 22A-22E, having varying placements of the association indicator and, in some implementations, an association button 170. It should be noted that the association indicator 34 and/or the association button 170 may be provided as a built-in feature of the detector or, alternatively, may be provided as a retrofittable add-on. Therefore, the association indicator 34 and association button 170 may be compatible with a variety of detectors. Further, some detectors, such as those lacking wireless capability, may be retrofit with a wireless communication interface, such as those mentioned above. Detector 22A is an embodiment of the detector 22 having only the association indicator 34. The association indicator 34 may be placed on the handle portion 172 of the detector 22A or on the body 174 of the detector 22A, for example at any of the four corners of the body 174 of the detector 22A. Detector 22B is an embodiment of the detector 22 having the association indicator 34 combined with the association button 170. That is, the association button may be a lit button that serves both an indication and initiation function. In detector 22B, the combined button is on the handle 172. Detector 2C is an embodiment of the detector 22 having the association button 170 on the handle 172 and the association indicator 34 placed on or within the detector body 174. Detector 22D is an embodiment of the detector 22 having both the association indicator 34 and the association button 170 disposed on or within the handle 172 as discrete features. Detector 22E is an embodiment of the detector 22 having the association indicator 34 disposed on or within the handle 172 while the association button 170 is placed on or within the body 174. Detector 22F is an embodiment of the detector 22 having the association indicator 34 and the association button 170 as a combined feature that is disposed on or within the body 174 of the detector 22F. It should be noted that while the above description provides examples of where the association indicator 34 and/or the association button may be placed on the detector 22, that many other configurations may be possible and are considered to be within the scope of the present disclosure.

Figure 7:
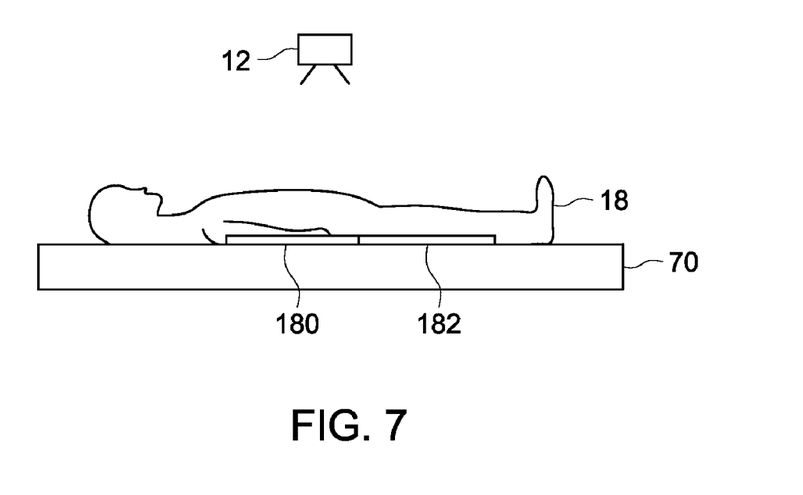
FIG. 7 is a schematic representation of a patient undergoing an imaging procedure that utilizes two detectors to increase an imaging area, in accordance with the present disclosure.

The ability of the X-ray system 10 to associate wireless subsystems may or may not be limited to one detector 22 being associated with the imaging subsystem 30. For example, it may be desirable to associate two or more detectors 22 under certain circumstances, such as trauma situations. In such situations, medical personnel may prefer to move the injured person as little as possible. The ability to combine the image data provided by multiple detectors 22 for example, to create an increased area of exposure, may reduce the need to move the injured person. FIG. 7 illustrates the use of more than one detector 22 in such situations. To perform such imaging, the patient 18 is placed on the table 70 underneath the X-ray source 26. Two associated detectors 180 and 182 are placed underneath the patient 18. Use of the imaging subsystem 30 as described above in such a setting allows a user to image a larger area (e.g., nearly twice as large) of the patient 18 compared to the use of a single detector 22.

As noted and described above, the present embodiments are directed towards providing methods for association and systems having respective components that are capable of performing association sequences. The sequences may include acts that both a user and the system (e.g., a controller) may perform. Such acts are described below with regard to FIG. 8, which is a process flow diagram depicting the acts performed by the user, and FIG. 9, which is a process flow diagram depicting the acts performed by the system 10.

Figure 8:
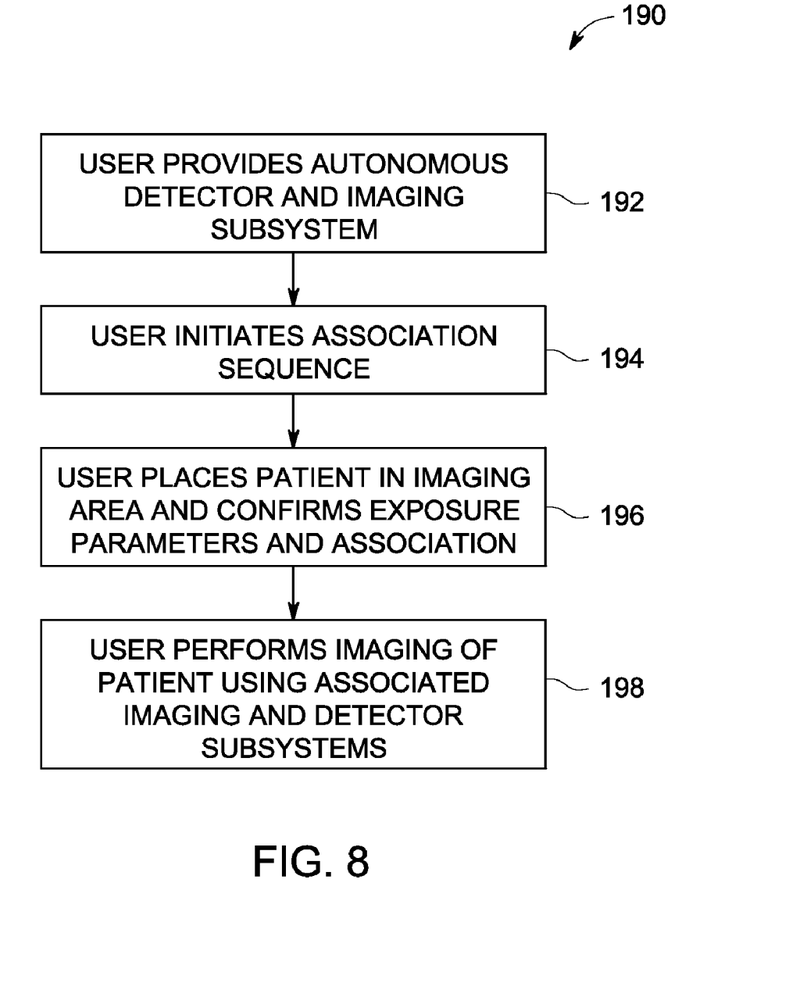
FIG. 8 is a process flow diagram of a workflow sequence performed by a user when operating an imaging system having autonomous subsystems.

The user (e.g., technician) may perform a set of sequences when imaging the patient 18, beginning with providing the imaging equipment and finishing with exposure of the patient 18 to generate images. An example workflow for the user is illustrated in FIG. 8. The imaging workflow 190 begins with the user providing the autonomous detector and imaging subsystems (block 192). The user may provide the subsystems by maneuvering a mobile imaging unit to a room or close to a patient bed or by directing the patient 18 to an imaging area, such as described in FIG. 2. The user may choose a specific detector or detectors to use in the imaging routine, and may initiate an association sequence (block 194). The association sequence initiation may include initiation at a workstation, initiation on either subsystem, such as via an association button, and the like. The user may perform acts such as scanning barcodes on either or both of the imaging and/or detector subsystems or passing a short range wireless transceiver of the detector 22 by a short range wireless transceiver of the imaging subsystem 30 to indicate which components are desired for association. Once a provisional association has been performed by the system, the user may confirm the association and exposure parameters for the particular imaging sequence (block 196). The association confirmation may be performed at a workstation, on either or both subsystems, or on a separate handheld device, as mentioned above. As an example, a pop-up window or similar indication may be provided at the display 40 of the workstation 38 listing the name or serial number of the associated detector 22 and imager subsystem 30. The user may confirm by accepting the alert, or may correct the association by re-initiating the association until the desired components are indicated. Upon confirmation by the user, the system may allow exposure at the user's discretion. Therefore, it should be noted that the system may not allow exposure prior to such confirmation. The user then performs imaging of the patient 18 using the associated imaging and detector subsystems (block 198).

Figure 9:
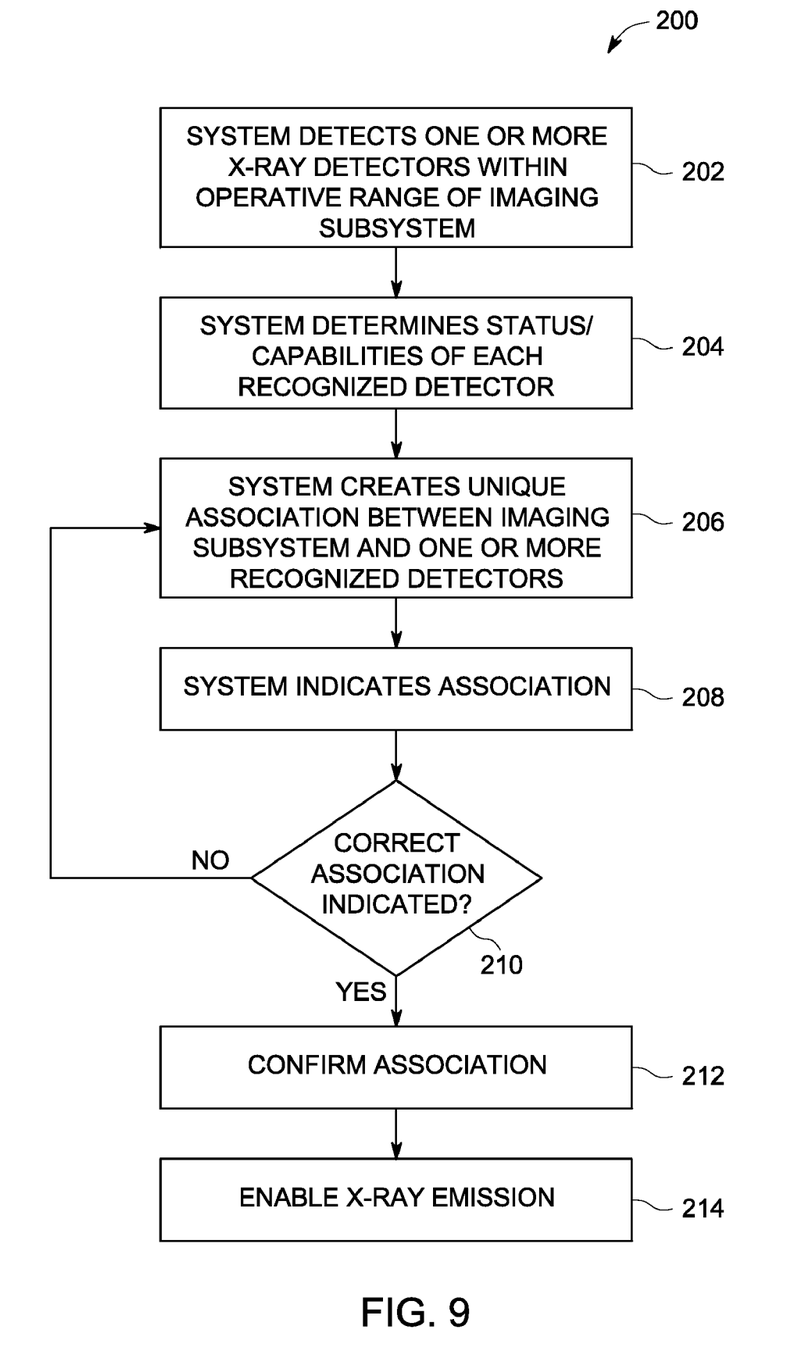
FIG. 9 is a process flow diagram of an association sequence performed by the system of FIGS. 1-4 and 8.

An association sequence 200, such as that performed by the system (e.g., system 10 of FIGS. 1 and 2) and initiated by the user (block 194 of FIG. 8) is illustrated as a process flow diagram in FIG. 9. After the user initiates the association sequence 200, the system 10 detects one or more X-ray detectors 22 within operative range of the imaging subsystem 30 (block 202). The system 10 may then determine the status (e.g., charge status, current associations) and/or capabilities (e.g., stored protocols, compatibilities) of each detector 22 (block 204). As the user indicates which detector 22 or detectors 22 are desired for association, the system 10 creates a unique association between the imaging subsystem 30 and one or more of the recognized and identified detectors 22 (block 206). The association is then indicated (block 208), for example on the one or more detectors 22, on the imaging subsystem 30, and so on. Further, it should be noted that the association may also be indicated on a display, such as the display 40 that is connected to the workstation 38 (FIG. 2). The system 10 may then prompt a user for input to determine if the correct association has been indicated (block 210). In embodiments where the provisional association is incorrectly indicated, the sequence may provide for the system 10 to re-create the unique association (block 206). Conversely, in embodiments where the association is correctly indicated, the association is confirmed (block 212) and X-ray emission is enabled (block 214).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of operation of an X-ray imaging system, comprising:
    creating an association between an autonomous imaging subsystem and an autonomous detector subsystem; and
    providing a user-perceptible indication of the association on the autonomous imaging subsystem, the autonomous detector subsystem, or both.

2. The method of claim 1, comprising receiving a user confirmation of the association between the autonomous imaging subsystem and the autonomous detector subsystem.

3. The method of claim 2, comprising disabling X-ray emission by one or more X-ray sources of the autonomous imaging subsystem until the association is created or until the user confirmation is received.

4. The method of claim 2, comprising providing a user-perceptible indication on the autonomous imaging subsystem that is comparable with an indication on the autonomous detector subsystem to enable the confirmation.

5. The method of claim 1, wherein creating the association comprises communicating an identifying signal of the autonomous imaging subsystem to the autonomous detector subsystem and communicating an identifying signal of the autonomous detector subsystem to the autonomous imaging subsystem; recognizing the respective identifying signals; and linking the autonomous imaging subsystem and the autonomous detector subsystem via a wireless interface based on the respective identifying signals.

6. The method of claim 5, wherein the respective identifying signals are generated by scanning indicia provided on the autonomous imaging subsystem and the autonomous detector.

7. The method of claim 6, wherein the indicia comprise one or more barcodes.

8. The method of claim 6, comprising communicating the indentifying signals from a scanning device to one or both of the autonomous imaging subsystem and the autonomous detector subsystem.

9. The method of claim 1, wherein providing a user-perceptible indication of the association comprises providing a visible, an audible, or a tactile indication, or any combination thereof, on both subsystems.

10. The method of claim 1, wherein providing a user-perceptible indication of the association comprises providing a visible, an audible, or a tactile indication, or any combination thereof, on only the detector subsystem.

11. The method of claim 1, wherein the autonomous detector subsystem is one of a plurality of autonomous detector subsystems that are within a range and capable of operating with the autonomous imaging subsystem.

12. A method of operation of an X-ray imaging system, comprising:
    associating an X-ray imaging subsystem and an X-ray detector subsystem;
    generating a user-perceptible indication of the association;
    receiving a user confirmation of the association; and
    imaging a subject with the X-ray imaging subsystem and the X-ray detector subsystem.

13. The method of claim 12, wherein associating the X-ray imaging subsystem and the X-ray detector subsystem comprises:
    wirelessly providing an identifying signal of the X-ray imaging subsystem to the X-ray detector subsystem; and
    wirelessly providing an identifying signal of the X-ray detector subsystem to the X-ray imaging subsystem.

14. The method of claim 13, comprising disabling X-ray emission by one or more X-ray sources of the imaging subsystem until the association is established or until the user confirmation is received.

15. The method of claim 12, comprising providing a user-perceptible indication on the imaging subsystem that is comparable with an indication on the detector subsystem to enable the confirmation.

16. The method of claim 12, wherein the X-ray detector subsystem comprises an autonomous detector subsystem that is one of a plurality of detector subsystems that are within a range and capable of operating with the X-ray imaging subsystem.

17. An X-ray imaging system comprising:
an autonomous imaging subsystem capable of operation with one or a plurality of autonomous detector subsystems;
a plurality of autonomous detector subsystems capable of operation with the autonomous imaging subsystem; and
wherein at least one of the autonomous imaging subsystem and the autonomous detector subsystems is configured to create an operative association between the autonomous X-ray imaging subsystem and one of the autonomous detector subsystems, the association permitting wireless exchange of imaging data, and to generate a user-perceptible indication of the association.

18. The system of claim 17, wherein at least one of the autonomous imaging subsystem and the autonomous detector subsystems is configured to provide a user-perceptible indication of the association and to receive a user confirmation of the association.

19. The system of claim 18, wherein the autonomous imaging subsystem is configured to disable emission of X-rays from an X-ray source until the association is created or until the confirmation is received.

20. The system of claim 18, wherein the autonomous imaging subsystem is configured to provide a user-perceptible indication on the autonomous imaging subsystem that is comparable with an indication on the detector subsystem to enable the confirmation.

21. A method, comprising:
creating an association between an autonomous imaging subsystem and an autonomous detector subsystem;
providing a user-perceptible indication of the association on the autonomous imaging subsystem, the autonomous detector subsystem, or both; and
before the association is created, providing a user-perceptible indication on the autonomous imaging subsystem, the autonomous detector subsystem, or both indicating that no association exists between the autonomous imaging subsystem and the autonomous detector subsystem.

22. The method of claim 21, wherein the user-perceptible indication of the association comprises providing a visible, an audible, or a tactile indication, or any combination thereof, on both subsystems.

23. The method of claim 21, wherein the user-perceptible indication of the association comprises illuminating a light of a first color, and the indication that no association exists comprises illuminating a light of a second, different color.

24. The method of claim 21, comprising receiving a user confirmation of the association between the autonomous imaging subsystem and the autonomous detector subsystem.

25. The method of claim 24, comprising providing a user-perceptible indication of the user confirmation, and wherein the user-perceptible indication of the user confirmation is different from the user-perceptible indication of the association.

* * * * *